United States Patent [19]

Revici

[11] Patent Number: 4,851,437

[45] Date of Patent: Jul. 25, 1989

[54] TUNG OIL COMPOSITIONS AND USE FOR TREATMENT OF BODY DEFICIENCIES

[75] Inventor: Emanuel Revici, New York, N.Y.

[73] Assignee: Elena Avram, New York, N.Y.

[21] Appl. No.: 895,963

[22] Filed: Aug. 12, 1986

[51] Int. Cl.[4] .................... A61K 31/215; A61K 31/20
[52] U.S. Cl. ..................................... 514/529; 514/560; 514/824; 514/886; 514/908; 514/924; 106/221; 106/243
[58] Field of Search ............... 514/560, 529, 824, 878, 514/886, 968, 924; 106/221, 243

[56] References Cited

U.S. PATENT DOCUMENTS 2,838,422  6/1958  Orthner et al. ...................... 106/243
4,152,416  5/1979  Spitzer et al. .......................... 424/46

Primary Examiner—John W. Rollins
Attorney, Agent, or Firm—Pennie & Edmonds

[57] ABSTRACT

Various tung oil or tung oil fatty acid compositions and use thereof for treating at least some symptoms of body defense deficiencies in patients having said symptoms.

17 Claims, No Drawings

TUNG OIL COMPOSITIONS AND USE FOR TREATMENT OF BODY DEFICIENCIES

TECHNICAL FIELD

The present invention concerns various tung oil compositions and their use in methods for treating and preventing the symptoms of different body deficiencies.

DETAILED DESCRIPTION OF THE PREFERRED EMBODIMENTS

I have found that the abnormal in general results from the incapacity, qualitative or quantitative, of the body to resolve the problem resulting from the intervention of a noxious action. I have found that this deficiency concerns the incapacity of the body defense to fight successfully the occuring condition related to the intervention of lipids, and for certain conditions, more specifically of agents having in their molecules a trienic conjugated formation.

I have found that the naturally very efficient defense agents concern fatty acids which have in their molecule three trienic conjugated double bonds formation, respectively three double bonds separated by single bonds. The parallel position of these conjugated trienes especially when part of a fatty acid gives the agent a marked efficient defense activity.

I have found that a such fatty acid represented by the eleostearic acid, is naturally present in tung oil (china wood oil) obtained from the seeds of Aleuritis Cordata. I have found that the use of the tung oil itself, with esters of this acid and also with other fatty acids present represents an active, and in the same time, an especially favorable accepted form to be administered.

The study of the pathological conditions has shown that a fatty acid defense deficiency is exhibited by a large number of them. They are specifically indicated for the administration of the tung oil. The following pathological conditions and their symptoms represent conditions with such a trienic fatty acids deficiency that can be treated accordingly to the invention: neoplastic diseases such as cancer, sarcoma, lymphoma and leukemia; infections, microbial, fungal and especially viral as in Ebstein - Barr, AIDS, the common cold, influenza and herpes; pain, especially acid pain; aging; arteriosclerosis; hypertension; organ inflammatory conditions convulsions and epilepsy; certain allergies; constipation; manic manifestations and schizophrenia. This enumeration is not limitative, any pathological condition with an anabolic-constructive imbalance representing a special indication for this treatment. In view of the nature of the treatment, according to the invention, the addition of other fats or fatty acids, especially those from polyunsaturated oils, enhances the activity of the tung oil.

The association of these polyunsaturated oils or their fatty acids with the tung oil or its ester compounds, through a common activity represents a progress in their use. Safflower oil, corn oil, cod liver oil, sardine and salmon oils, their fatty acids or other unsaturated fatty acids added to the tung oil enhances its defense activity The eleostearic acid or its salts or esters and the tung oil fatty acids obtained from the tung oil through any procedure are other forms of returning to the body the missing defense lipids which cause the deficiency.

The basic nature of the intervention through an induced natural defense has led to the administration of the agents of this invention also for the general prevention of a diversity of conditions resulting from their deficiency. Cancer, arteriosclerosis and aging represent the main conditions considered to be prevented by the agents of the invention.

The main defect of the use of tung oil, its compounds, its fatty acids, or the eleostearic acid is the induction of diarrhea. The administration by injection reduces this problem, but does not prevent it, especially at higher dosages. The addition of commonly available antidiarrhea preparations, especially those limited to a local intestinal action, may permit the use of higher doses, especially for the administration by injection. The addition of the tung oil of other antianabolic compounds especially indicated for the condition treated, is manifestly enhancing its favorable action. Such compounds comprise mainly bivalent negative selenium, bivalent negative sulfur, 3-ketones, fatty acids, fatty aldehydes, with or without copper, barium and magnesium incorporated therein. This enumeration is not limitative.

In view of the relationship between defense and the agents of the invention, good effects were seen also in conditions with opposite catabolic imbalance, especially when treated together with anticatabolic agents, especially non sterolic. The oxidation of the tung oil may even enhance its activity The toxicity studies - acute, subacute and chronic in mice, rats, guinea pigs, hamsters and rabbits has shown an acceptance of doses between 500 and and 2000 times higher than those respectively taken by humans, which represents a fairly good condition. No pathological changes and no carcinogenic action were seen.

The usual doses for the different conditions vary according to the condition, with usual daily doses orally and by injection, from 50 mg of the oil to more than 500 mg. These doses are generally administered twice a day or more frequently, if necessary.

The administration of these formulations are in general limited by the appearance of diarrhea. Due to the unique mechanism of intervention, through the induction of the main natural defense, the inventions opens a new, very broad way in prevention and therapy.

The following examples illustrate the invention. The percentages shown are by weight.

EXAMPLE 1

Tung oil 20%
Safflower oil 80%
For oral administration: 50 mg to 500 mg oil mixture per dose given twice per day

EXAMPLE 2

Tung oil 5%
Safflower oil 95%
Sterile for injection: same amounts as Example 1.

EXAMPLE 3

Tung oil fatty acid 20%
Corn oil fatty acid 20%
Safflower oil 60%
For oral administration: same amounts as Example 1.

EXAMPLE 4

Tung oil fatty acid 5%
Safflower oil 95%
Sterile for injection: same amounts as Example 1.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for treating the symptoms of a body deficiency cause by an anabolic-constructive imbalance without treating the deficiency itself which comprises administrating an amount of between 50 and 500 mg of a pharmaceutical composition comprising a mixture of tung oil, an ester of a tung oil fatty acid or an ester of eleostearic acid in an amount of between about 50 to 50 weight percent, and a polyunsaturated oil or an ester of a polyunsaturated fatty acid in an amount of between 50 and 95 weight percent to a patient who is suffering from the symptoms of said deficiency for a sufficient time to alleviate at least one of said symptoms.

2. The method of claim 1 wherein said amount is administered orally or by injection.

3. The method of claim 1 wherein the amount is administered twice daily.

4. A method for treating the symptoms of a body deficiency caused by an anabolic-constructive imbalance without treating the deficiency itself which comprises administering an amount of between 50 and 500 mg of a pharmaceutical composition comprising a mixture of tung oil, an ester of a tung oil fatty acid or an ester of eleostearic acid in an amount of between about 5 and 50 weight percent and one of corn oil, safflower oil, cod liver oil, salmon oil or a mixture thereof in an amount of between 50 and 95 weight percent to a patient who is suffering from the symptoms of said deficiency for a sufficient time to alleviate at least one of said symptoms.

5. The method of claim 4 wherein said amount is administered orally or by injection.

6. The method of claim 7 wherein the amount is administered twice daily.

7. A method for treating the symptoms of a body deficiency caused by an anabolic-constructive imbalance without treating the deficiency itself which comprises administering an amount of between 50 to 500 mg of a pharmaceutical composition comprising a mixture of between 5 to 25 weight percent tung oil or an ester of a tung oil fatty acid; between 5 and 25 weight percent of corn oil; and between 50 and 90 weight percent of safflower oil, cod liver oil, sardine oil, salmon oil, or mixtures thereof to a patient who is suffering from the symptoms of said deficiency for a sufficient time to alleviate at least one of said symptoms.

8. The method of claim 7, wherein said amount is administered orally or by injection.

9. The method of claim 7, wherein the amount is administered twice daily.

10. A method for counteracting the symptoms of deficiencies in a human body caused by a reduced lipidic content in the body dut to an anabolic-constructive imbalance which comprises administering to said body a sufficient amount of a compound having at least one trienic conjugated formation of the type—CH? CH-CH? CH-CH? CH- in combination with one of a polyunsaturated oil or an ester of a polyunsaturated fatty acid to restore the lipidic content of the body to a normal or elevated level.

11. The method of claim 10, wherein the compound having a trienic configuated formation is an ester of eleostearic acid, an ester of a tung oil fatty acid, or tung oil.

12. The method of claim 11 wherein the amount to be administered is between 50 and 500 mg.

13. The method of claim 12 wherein said amount is administered orally or by injection.

14. The method of claim 13 wherein the amount is administered twice daily.

15. The method of claim 10 wherein the polyunsaturated oil is corn oil, safflower oil, cod liver oil, sardine oil, salmon oil or mixtures thereof.

16. The method of claim 10 wherein the compound having a trienic conjugated formation is present in an amount of between 5 and 50 percent with the polyunsaturated compound being present in an amount of between 50 and 95 weight percent.

17. The method of claim 15 wherein the compound having a trienic compound is present in an amount of between 5 and 25 weight percent and the polyunsaturated oil is a mixture of corn oil in an amount between 5 and 25 weight percent and a fish oil in an amount of between 50 and 90 weight percent.

* * * * *